United States Patent
Park et al.

(10) Patent No.: US 11,365,218 B2
(45) Date of Patent: Jun. 21, 2022

(54) BIFUNCTIONAL PEPTIDE HAVING CAPABILITY TO REDUCE INFLAMMATION AND CAPABILITY TO FACILITATE DIFFERENTIATION OF STEM CELLS INTO CHONDROCYTES AND USE THEREOF

(71) Applicants: Seoul National University R&DB Foundation, Seoul (KR); Nano Intelligent Biomedical Engineering Corporation Co. Ltd., Chungcheongbuk-do (KR)

(72) Inventors: Yoon Jeong Park, Seoul (KR); Chong-Pyoung Chung, Seoul (KR); Jue-Yeon Lee, Gyeonggi-do (KR)

(73) Assignees: SEOUL NATIONAL UNIVERSITY R&DB FOUNDATION, Seoul (KR); NANO INTELLIGENT BIOMEDICAL ENGINEERING CORPORATION CO. LTD., Chungcheongbuk-Do (KR)

( * ) Notice: Subject to any disclaimer, the term of this patent is extended or adjusted under 35 U.S.C. 154(b) by 0 days.

(21) Appl. No.: 16/882,648

(22) Filed: May 25, 2020

(65) Prior Publication Data

US 2020/0283481 A1   Sep. 10, 2020

Related U.S. Application Data (62) Division of application No. 16/297,670, filed on Mar. 10, 2019, now abandoned.

(30) Foreign Application Priority Data

Mar. 14, 2018 (KR) ................. 10-2018-0029912

(51) Int. Cl.
| | | |
|---|---|---|
| C07K 7/08 | (2006.01) | |
| A61P 19/02 | (2006.01) | |
| A61L 27/54 | (2006.01) | |
| A61K 38/10 | (2006.01) | |
| A61L 27/22 | (2006.01) | |
| A61K 38/00 | (2006.01) | |

(52) U.S. Cl.
CPC ............. *C07K 7/08* (2013.01); *A61K 38/10* (2013.01); *A61L 27/227* (2013.01); *A61L 27/54* (2013.01); *A61P 19/02* (2018.01); *A61K 38/00* (2013.01); *A61L 2300/25* (2013.01); *A61L 2300/41* (2013.01)

(58) Field of Classification Search
CPC ..... A61K 38/00; A61K 38/10; A61L 2300/25; A61L 2300/41; A61L 27/227; A61L 27/54; A61P 19/02; C07K 7/08
See application file for complete search history.

(56) References Cited

U.S. PATENT DOCUMENTS

| | | | | |
|---|---|---|---|---|
| 2010/0016231 A1* | 1/2010 | Kjaer | ...................... | A61P 31/00 514/1.1 |
| 2010/0016232 A1 | 1/2010 | Kjaer et al. | | |
| 2013/0210707 A1* | 8/2013 | Chung | ............... | A61K 38/1858 514/2.4 |
| 2017/0275594 A1 | 9/2017 | Park et al. | | |
| 2019/0284237 A1 | 9/2019 | Park et al. | | |

FOREIGN PATENT DOCUMENTS

| | | |
|---|---|---|
| EP | 2583684 A2 | 4/2013 |
| EP | 3111951 A | 1/2017 |
| WO | 2016153185 A1 | 9/2016 |

OTHER PUBLICATIONS

Priyanka Agarwal, Injectable implants for the sustained release of protein and peptide drugs, Drug Discovery Today vol. 18, Nos. 7/8, Apr. 2013.*
K.S. Kim, Injectable hyaluronic acid-tyramine hydrogels for the treatment of rheumatoid arthritis, Acta Biomaterialia 7 (2011) 666-674.*
Biological implant | definition of biological implant by Medical dictionary https://medical-dictionary.thefreedictionary.com/biological+implant, accessed on Oct. 14, 2020, p. 1.*
BlueCross MN, How to Prevent Arthritis Pain, https://www.bluecrossmn.com/wellbeing/preventive-care/how-prevent-arthritis-pain , accessed on Oct. 14, 2020, pp. 1-7.*
Sergei S Makarov, NF-κB in rheumatoid arthritis: a pivotal regulator of inflammation, hyperplasia, and tissue destruction, Arthritis Res 2001, 3:200-206.*
MayoClinic, Osteoarthritis vs, rheumatoid arthritis, published online 2009.*
UniProtKB—P81534 (D103A_HUMAN), accessed Apr. 2, 2020 and cited in parent U.S. Appl. No. 16/297,670.
Blagojevic, M., et al., "Risk Factors for Onset of Osteoarthritis of the Knee in Older Adults: A Systematic Review and Meta-Analysis", "Osteoarthritis and Cartilage", 2010, pp. 24-33, vol. 18.
Felson, D.T., et al., "Osteoarthritis: New Insights Part 1: The Disease and its Risk Factors", "Annals of Internal Medicine", Oct. 17, 2000, pp. 635-646, vol. 133, No. 8.

(Continued)

*Primary Examiner* — Julie Ha
*Assistant Examiner* — Erinne R Dabkowski
(74) *Attorney, Agent, or Firm* — Hultquist, PLLC; Steven J. Hultquist (57) ABSTRACT

Disclosed are a bifunctional peptide having the capability to reduce inflammation and the capability to facilitate differentiation of stem cells into chondrocytes and the use thereof. Advantageously, the bifunctional peptide is useful for the prevention or treatment of arthritis accompanied by inflammation and damage of cartilage tissue due to excellent effects of reducing inflammation and facilitating differentiation of stem cells into chondrocytes, can be easily applied to various surgical regenerative treatments including orthopedic treatments, and can shorten the treatment period.

9 Claims, 3 Drawing Sheets
Specification includes a Sequence Listing.

(56) References Cited

OTHER PUBLICATIONS

Gay, S., et al., "Molecular and Cellular Mechanisms of Joint Destruction in Rheumatoid Arthritis: Two Cellular Mechanisms Explain Joint Destruction?", "Annals of the Rheumatic Diseases", 1993, pp. S39-S47, vol. 52.

Lee, J.Y., et al., "Identification of a Cell-Penetrating Peptide Domain From Human Beta-Defensin 3 and Characterization of its Inflammatory Activity", "International Journal of Nanomedicine", 2015, pp. 5423-5434, vol. 10.

Varoga, D., et al., "Human Beta-Defensin 3 Mediates Tissue Remodeling Processes in Articular Cartilage by Increasing Levels of Metalloproteinases and Reducing Levels of Their Endogenous Inhibitors", "Arthritis and Rheumatism", Jun. 2005, pp. 1736-1745, vol. 52, No. 6.

\* cited by examiner

BIFUNCTIONAL PEPTIDE HAVING CAPABILITY TO REDUCE INFLAMMATION AND CAPABILITY TO FACILITATE DIFFERENTIATION OF STEM CELLS INTO CHONDROCYTES AND USE THEREOF

CROSS-REFERENCE TO RELATED APPLICATION

This is a divisional under 35 USC § 120 of U.S. patent application Ser. No. 16/297,670, which in turn claims priority under 35 USC § 119 of Korean Patent Application No. 10-2018-0029912 filed Mar. 14, 2018. The disclosures of of U.S. patent application Ser. No. 16/297,670 and Korean Patent Application No. 10-2018-0029912 are hereby incorporated herein by reference in their respective entireties, for all purposes.

TECHNICAL FIELD

The present invention relates to a bifunctional peptide having the capability to reduce inflammation and the capability to facilitate differentiation from stem cells into chondrocytes and the use thereof. More particularly, the present invention relates to a peptide represented by an amino acid sequence of any one of SEQ ID NOS: 1 to 8, a pharmaceutical composition for preventing or treating arthritis and a biomaterial for treating arthritis comprising the same.

BACKGROUND ART

Damage to cartilage tissue constituting joints may cause arthritis accompanied by swelling, fever and pain. Arthritis is classified into about 100 or more types depending on the cause thereof. The most common type of arthritis is osteoarthritis, which is a degenerative joint disease mainly caused by aging, and other types of arthritis include rheumatoid arthritis and psoriatic arthritis, which are autoimmune diseases, septic arthritis due to infection and the like.

Osteoarthritis is a disease in which the joint cartilage surrounding the joint surface of the bone is worn out, the bone under the cartilage is exposed, and the synovium around the joint is inflamed, resulting in pain and deformation. The joints have soft cartilage serving as a buffer and this results from changes of cartilage due to aging, improper mechanical pressure, genetic causes, obesity, trauma to the joints, and cartilage damage due to inflammation (Blagojevic, M. et al., Osteoarthritis Cartilage 18: 24-33 (2010). Felson, D. T. et al., Osteoarthritis: new insights. Part 1: The Disease and its risk factors. Ann Intern Med 133: 635-646 (2000).).

Rheumatoid arthritis is a type of autoimmune disease in which the body's immune system attacks itself and the synovial membrane surrounding the joints is inflamed, and may develop in all age groups from infants to the elderly (Gay S, et al., Ann. Rheum. Dis. 52: S39-S40 (1993)).

Cartilage is a tissue including only a cartilage cell, as a single cell, and an extracellular matrix, and is susceptible to wear with aging. The cartilage cell is surrounded by the rigid extracellular matrix and thus is difficult to regenerate once damaged or degenerated.

Currently, analgesics, steroids, and nonsteroidal anti-inflammatory drugs, which are drugs used to treat damaged cartilage, only nonspecifically relieve pain and inflammation, but have no fundamental therapeutic effect. Cartilage protectants such as hyaluronic acid, glucosamine and chondroitin only function to temporarily protect the joints by alleviating impacts. Bone marrow stimulation, which is a clinical surgical method used in the orthopedic surgery, is a method of filling cartilage damage with a blood clot containing stem cells derived from bone marrow and has an advantage in that a surgery process is relatively easy and simple. However, the method is disadvantageous in that, after surgery, the damaged cartilage is regenerated as fibrous cartilage rather than hyaline cartilage. Bone-cartilage tissue grafting is a method of collecting bone-cartilage connective tissue in the site with a less weight from the patient's own cartilage tissue and then implanting the bone-cartilage connective tissue into the damaged cartilage site. Disadvantageously, this method cannot be used to treat large cartilage damage sites.

In order to overcome this disadvantage, efforts are being made to regenerate cartilage using stem cells, scaffolds and growth factors, which are three major components of tissue engineering. However, it is difficult for stem cells injected alone into the damaged cartilage sites to survive and differentiate. In order to solve this problem, a method of transferring cells using polymer-based scaffolds is used, but the scaffolds may disadvantageously cause a spatial limitation, when the cells proliferate in the scaffolds or when the extracellular matrix is secreted. Thus, the method of completely regenerating damaged cartilage remains incomplete.

In the case of cartilage damage accompanied by inflammation such as osteoarthritis and rheumatoid arthritis, it is difficult to regenerate cartilage without treating the inflammation, although various techniques for cartilage regeneration are attempted. Therefore, two functions of inflammation treatment and cartilage regeneration are needed.

Histone deacetylase (HDAC) is an enzyme that deacetylates histones to condense chromatin and inhibit gene transcription. A histone protein is an element that constitutes the nucleosome with DNA. The structure of the histone protein can be variously modified. Histone acetylation and methylation, along with DNA methylation, are important acquired mechanisms to regulate the expression of certain genes. In general, when the expression of the certain genes is activated, the histone tail is acetylated by histone acetyltransferase (HAT), whereas, when the histone tail is deacetylated by histone deacetylase, i.e., HDAC, the expression of certain genes is inactivated, that is, gene expression is inhibited.

The roles of HDACs in treating a variety of diseases, including inflammatory diseases and degenerative diseases including neuropathy, and modulators thereof have been studied. Previous studies have shown that HDAC inhibitors are effective not only in treating inflammation, but also in facilitating specific differentiation of stem cells into nerve, bone and liver tissues. However, there are no peptide-based HDAC inhibitors other than low molecular-weight synthetic substances and hereditary substances such as siRNA.

Accordingly, as a result of intensive studies to solve the problems of the prior art as described above, the present inventors have found a specific peptide, which is capable of facilitating differentiation of stem cells into chondrocytes while reducing inflammation of joint by inhibiting the expression of HDAC and the production of cytokine interleukin 6, and have completed the present invention on the basis thereof.

DISCLOSURE

Technical Problem

Therefore, it is one object of the present invention to provide a bifunctional peptide having the capability to reduce inflammation and the capability to facilitate differentiation of stem cells into chondrocytes.

It is another object of the present invention to provide a pharmaceutical composition for preventing or treating arthritis comprising the bifunctional peptide.

It is another object of the present invention to provide a biomaterial for treating arthritis comprising the bifunctional peptide.

Technical Solution

In accordance with the present invention, the above and other objects can be accomplished by the provision of a bifunctional peptide represented by an amino acid sequence of any one of SEQ ID NOS: 1 to 8.

In accordance with another aspect of the present invention, provided is a pharmaceutical composition for preventing or treating arthritis comprising the bifunctional peptide as an active ingredient.

In accordance with yet another aspect of the present invention, provided is a biomaterial for treating arthritis comprising the bifunctional peptide.

In accordance with another aspect of the present invention, provided is a method for preventing or treating arthritis comprising administering to the subject the bifunctional peptide.

In accordance with another aspect of the present invention, provided is the bifunctional peptide for use in a method of preventing or treating arthritis.

In accordance with another aspect of the present invention, provided is a pharmaceutical composition comprising the bifunctional peptide for use in a method of preventing or treating arthritis.

In accordance with another aspect of the present invention, provided is a use of the bifunctional peptide for the manufacture of a medicament for preventing or treating arthritis.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Unless defined otherwise, all technical and scientific terms used herein have the same meanings as appreciated by those skilled in the field to which the present invention pertains. In general, the nomenclature used herein is well-known in the art and is ordinarily used.

In the present invention, the experiment was carried out by preparing a bifunctional peptide having the capability to facilitate the differentiation of stem cells into chondrocytes and the capability to reduce inflammation, and then treating RAW 264.7 cells and mesenchymal stem cells (MSCs) having inflammation induced by LPS (lipopolysaccharide) with the bifunctional peptide. As a result, it was found that the expression of HDAC1 and HDAC5 and the production of inflammatory cytokine interleukin 6 (IL-6) were decreased and that the expression of cartilage-cell-specific genes was increased.

Accordingly, in one aspect, the present invention is directed to a peptide represented by an amino acid sequence of any one of SEQ ID NOS: 1 to 8.

SEQ ID NO: 1:
GKCSTRGRKCCRRKK

SEQ ID NO: 2:
GKCSTRGRKCMRRKK

SEQ ID NO: 3:
GKCSTRGRKMCRRKK

SEQ ID NO: 4:
GKCSTRGRKMMRRKK

SEQ ID NO: 5:
GKMSTRGRKCCRRKK

SEQ ID NO: 6:
GKMSTRGRKMCRRKK

SEQ ID NO: 7:
GKMSTRGRKCMRRKK

SEQ ID NO: 8:
GKMSTRGRKMMRRKK

In the present invention, SEQ ID NO: 2 is obtained by substituting cysteine of SEQ ID NO: 1 with methionine, wherein such substitution aims at preventing oxidation in the SS bond present in adjacent cysteine-cysteine or distant cysteine-cysteine structures. The total number of cysteines in SEQ ID NO: 1 is 3, and SEQ ID NOS: 2 to 8 are obtained by substituting these cysteines with methionine.

In the present invention, the peptide may have dual functions including the capability of reducing inflammation and the capability of facilitating differentiation of stem cells into chondrocytes.

In the present invention, the peptide is preferably produced through a solid-phase peptide synthesis, when taking into consideration the fact that the peptide can be produced in a large amount compared to a protein produced by a recombinant DNA technique, but the present invention is not limited thereto.

Meanwhile, the present inventors have found through in-vitro experiments that the peptide can reduce the inflammation of cells and the capability to facilitate differentiation of stem cells into chondrocytes.

In another aspect, the present invention is directed to a pharmaceutical composition for preventing or treating arthritis comprising the bifunctional peptide as an active ingredient.

As used herein, the term "composition" is considered to include any product containing a certain ingredient as well as any product that is prepared directly or indirectly by a combination of certain ingredients.

In the present invention, the composition may further contain a pharmaceutically acceptable carrier, wherein the carrier is selected from the group consisting of saline, sterilized water, Ringer's solution, buffered saline, dextrose solution, maltodextrin solution, glycerol, and ethanol, but the present invention is not limited thereto.

In the present invention, the composition may further contain at least one adjuvant selected from the group consisting of an excipient, a buffer, an antimicrobial antiseptic, a surfactant, an antioxidant, a tonicity adjuster, a preservative, a thickener and a viscosity modifier, but the present invention is not limited thereto. Each ingredient can be selected from a raw material commonly used in the art and suitably modified and used within the range acceptable for the art.

In the present invention, the composition may be formulated into any one selected from the group consisting of injections, oral mucosa agents, capsules, transdermal agents and gel-type agents, but the present invention is not limited thereto, and can be prepared into a suitable formulation using a method well-known in the art (Joseph Price Remington, Remington's Pharmaceutical Science, 17th edition, Mack Publishing Company, Easton. Pa.).

In the present invention, the composition may be administered through a route commonly used in the pharmaceutical field, preferably parenteral administration. For example, the composition may be administered through an intravenous, intraperitoneal, intramuscular, intraarterial, oral, intracardiac, intramedullary, intrathecal, transdermal, intestinal, subcutaneous, sublingual or topical administration route. In general, the composition contains, as an active ingredient, a therapeutically effective amount of the bifunctional peptide having the capability to reduce inflammation activity and the capability to facilitate differentiation of stem cells into chondrocytes according to the present invention.

In the present invention, the preparation for topical administration may be in the form of a gel or film. The gel base preferably includes one or more selected from the group consisting of collagen, chitosan, hyaluronic acid, alginic acid, propylene glycol, propylene glycol alginate, poloxamer and chondroitin sulfate, but the present invention is not limited thereto.

In the present invention, the composition is preferably administered at a dose of 0.001 to 1,000 mg, more preferably 0.1 to 100 mg, per 1 kg of a body weight of the subject in need of treatment, but is not limited thereto, and the range of the dose may vary according to body weight, age, gender, a state of health and diet of a patient, administration time, administration method, excretion rate and severity of disease. The dose can be determined in consideration of these factors by an ordinary expert in the art.

In another aspect, the present invention is directed to a method for preventing or treating arthritis comprising administering to the subject the bifunctional peptide.

In another aspect, the present invention is directed to the bifunctional peptide for use in a method of preventing or treating arthritis.

In another aspect, the present invention is directed to a pharmaceutical composition comprising the bifunctional peptide for use in a method of preventing or treating arthritis.

In another aspect, the present invention is directed to a use of the bifunctional peptide for preventing or treating arthritis.

In another aspect, the present invention is directed to a use of the bifunctional peptide for the manufacture of a medicament for preventing or treating arthritis.

In another aspect, the present invention is directed to a biomaterial for treating arthritis comprising the bifunctional peptide.

In the present invention, in order to bind the bifunctional peptide sequence to the biomaterial, a chemical bond can be induced using a cross-linking agent. At this time, treatment is carried out to introduce a functional group, for example, a thiol group (—SH), which is capable of binding to the cysteine at the end of the peptide, or to form amine ($NH_2$), so that the bifunctional peptide can be smoothly applied to a cross-linking reaction using a cross-linking agent.

Examples of the crosslinking agent that can be used in the present invention include, but are not limited to, 1,4-bismaleimidobutane (BMB), 1,11-bismaleimidotetraethyleneglycol (BM[PEO]4), 1-ethyl-3-[3-dimethyl aminopropyl]carbodiimide hydrochloride (EDC), succinimidyl-4-[N-maleimidomethylcyclohexanel-carboxy-[6-amidocaproate]] (SMCC) and sulfonates thereof (sulfo-SMCC), succinimidyl 6-[3-(2-pyridyldithio)-propionamido] hexanoate (SPDP) and sulfonates thereof (sulfo-SPDP), m-maleimidobenzoyl-N-hydroxysuccinimide ester (MBS) and sulfonates thereof (sulfo-MBS), and succinimidyl [4-(p-maleimidophenyl) butyrate] (SMPB) and sulfonates thereof (sulfo-SMPB).

In the present invention, the biomaterial may include any one selected from the group consisting of a barrier membrane, a porous scaffold, and an implant for bio-implant produced in the form of a gel, but the present invention is not limited thereto. Any kind and form of barrier membrane, porous scaffold and gel used in the art can be used.

In the present invention, the barrier membrane is preferably selected from the group consisting of collagen, chitosan, gelatin, polylactide, polylactide glycolide and polycaprolactone, but the present invention is not limited thereto.

In addition, the porous scaffold may be any one selected from the group consisting of collagen, chitosan, gelatin, hyaluronic acid, alginic acid, chondroitin sulfate, polylactide, polylactide glycolide, and polycaprolactone, but the present invention is not limited thereto.

The gel is preferably selected from the group consisting of collagen, chitosan, gelatin, hyaluronic acid, alginic acid, poloxamer, propylene glycol, propylene glycol alginate, chondroitin sulfate and glycosaminoglycan, but the present invention is not limited thereto.

Hereinafter, the present invention will be described in more detail with reference to the following examples. However, it will be obvious to those skilled in the art that these examples are provided only for illustration of the present invention and should not be construed as limiting the scope of the present invention.

Example 1: Synthesis of Bifunctional Peptide Having Capability to Reduce Inflammation and Capability to Facilitate Differentiation of Stem Cells into Chondrocytes Bifunctional peptides (SEQ ID NOS: 1 to 8) having anti-inflammatory activity and the capability to facilitate differentiation of stem cells into chondrocytes were synthesized in a predetermined order from the N terminal through F-moc solid-phase peptide synthesis. The synthesized peptide sequences were cleaved from the resin, washed, lyophilized and then separated and purified by liquid chromatography. The molecular weights of the purified peptides were identified through a MALDI-TOF assay.

SEQ ID NO: 1:
GKCSTRGRKCCRRKK

SEQ ID NO: 2:
GKCSTRGRKCMRRKK

SEQ ID NO: 3:
GKCSTRGRKMCRRKK

SEQ ID NO: 4:
GKCSTRGRKMMRRKK

SEQ ID NO: 5:
GKMSTRGRKCCRRKK

SEQ ID NO: 6:
GKMSTRGRKMCRRKK

SEQ ID NO: 7:
GKMSTRGRKCMRRKK

SEQ ID NO: 8:
GKMSTRGRKMMRRKK

Example 2: Preparation of Pharmaceutical Composition for Preventing or Treating Arthritis Comprising Bifunctional Peptide Having Capability to Reduce Inflammation and Capability to Facilitate Differentiation of Stem Cells into Chondrocytes A pharmaceutical composition for preventing or treating arthritis comprising the bifunctional peptide having the capability to reduce inflammation and the capability to facilitate differentiation of stem cells into chondrocytes, as an active ingredient, was prepared (Table 1).

TABLE 1

| Ingredients | Weight(mg) |
| --- | --- |
| Bifunctional peptides (SEQ ID NOS: 1 to 8) | 1 |
| Sodium chloride, USP | 8.18 |
| Sodium succinate | 1.62 |
| WFI | 987.5 |
| Sodium hydroxide, NF and/or acetic acid, NF | |
| Total | 1 g, pH 6 |

Example 3: Production of Biomaterial for Treating Arthritis Including Bifunctional Peptide Having Capability to Reduce Inflammation and Having Capability to Facilitate Differentiation of Stem Cells into Chondrocytes The collagen biomaterial produced in the form of a barrier membrane or a porous scaffold was added to 2 ml of phosphate buffer solution (pH 7.4) to hydrate the surface thereof, sulfo-SMCC was added thereto as a crosslinking agent at a concentration of 5 mg/ml, and stirring was conducted for 2 hours to introduce a functional group into the surface of the biomaterial. After reaction at room temperature for 2 hours, the collagen biomaterial was washed, a solution of 10 mg of the peptide of SEQ ID NO: 4 in 100 μl of phosphate buffer was added thereto, reaction was conducted for 24 hours and the resulting product was then washed to produce a collagen biomaterial including an immobilized peptide.

Figure 1:
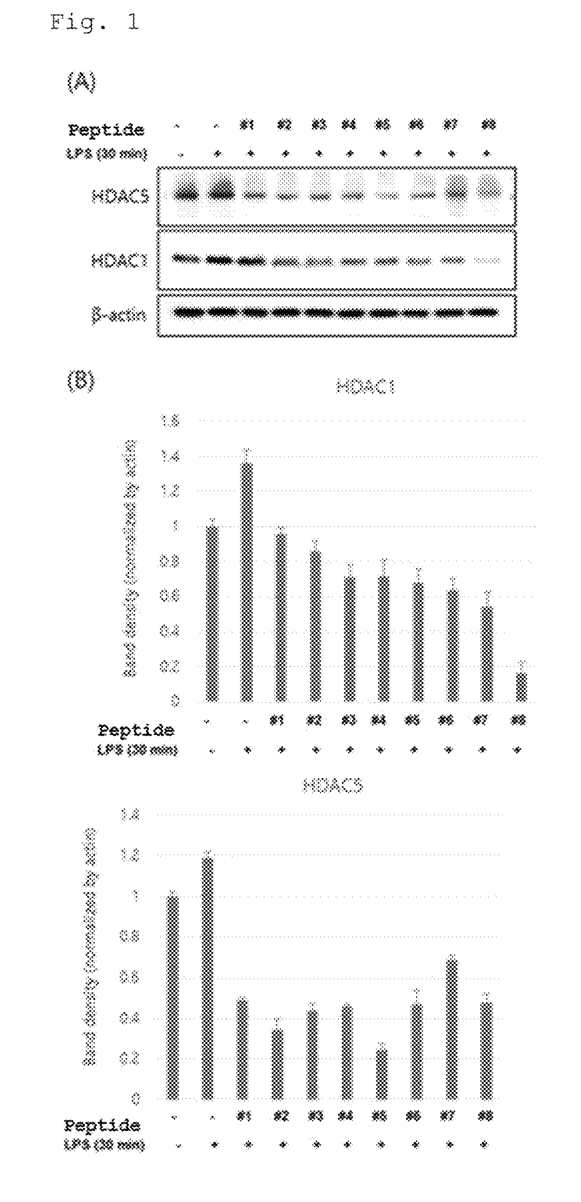
FIG. 1 show the results of Western blotting (A) and band density (B) to identify the degree of protein expression of HDAC1 and HDAC5 after treatment of RAW 264.7 cells with the peptides of SEQ ID NOS: 1 to 8 and then induction of inflammation by LPS (lipopolysaccharide).

Test Example 1: Evaluation of Inhibition of HDAC Expression by Bifunctional Peptide Having Capability to Reduce Inflammation and Capability to Facilitate Differentiation of Stem Cells into Chondrocytes In order to identify the change of HDAC expression by the bifunctional peptide at a molecular level, RAW 264.7 cells were plated at a density of 70% in a 6-well plate, and after hours, the RAW 264.7 cells were subjected to cell starvation in DMEM medium containing 0.5% FBS for 2 hours. After the cells were treated with medium containing 100 μM of each of the peptides of SEQ ID NOS: 1 to 8 for 1 hour, the cells were treated with LPS at a concentration of 1 μg/ml to induce an inflammatory reaction for 30 minutes. Proteins were lysed using RIPA lysis buffer (25 mM Tris-HCl pH 7.6, 150 mM NaCl, 1% NP-40, 1% sodium deoxycholate, 0.1% SDS) containing a protease inhibitor and a phosphatase inhibitor. Proteins were assayed by BCA protein assay, and expression levels of HDAC1 and HDAC5 proteins were identified through Western blotting (FIG. 1). For the Western blotting, the sample was loaded at a constant amount on an 8% SDS PAGE gel along with a size marker, centrifuged for about 2 hours and then transferred to a nitrocellulose membrane. The transferred membrane was blocked with 5% skim milk for 1 hour and was reacted with the first antibody at a ratio of 1:1000 overnight. Then, the membrane was washed with TBST containing 0.1% tween-20 and reacted with a HRP-coated secondary antibody for 1 hour and then chemiluminescence was identified with an ECL substrate.

FIG. 1 shows the results of Western blotting (A) to identify the expression levels of HDAC1 and HDAC5 proteins by the peptides of SEQ ID NOS: 1 to 8. FIG. 1 shows the results (B) of normalization of HDAC1 and HDAC5 bands by actin bands. The expression of HDAC 1 and HDAC5 was increased upon treatment with LPS alone, but the expression levels of HDAC1 and HDCA5 proteins were inhibited by the peptides when simultaneously treated with LPS and peptides of SEQ ID NOS: 1 to 8. It can be seen from these results that the peptides of SEQ ID NOS: 1 to 8 were effective as HDAC inhibitors.

Test Example 2: Evaluation of Inhibitory Effect on Production of Inflammatory Cytokine by Bifunctional Peptide Having Capability to Reduce Inflammation and Capability to Facilitate Differentiation of Stem Cells into Chondrocytes RAW 264.7 cells were seeded at a density of $5 \times 10^3$ cells/ml in a 24-well plate in order to identify the production of IL-6 by the bifunctional peptide. Each well was treated with each of the peptides of SEQ ID NOS: 1 to 8 at a concentration of 100 μM. After 1 hour, the well was treated with LPS at a concentration of 1 μg/ml and cultured for 17 hours. The concentration of IL-6 released from the cell culture medium was measured using an ELISA kit (R&D, Minneapolis, Minn., USA).

Figure 2:
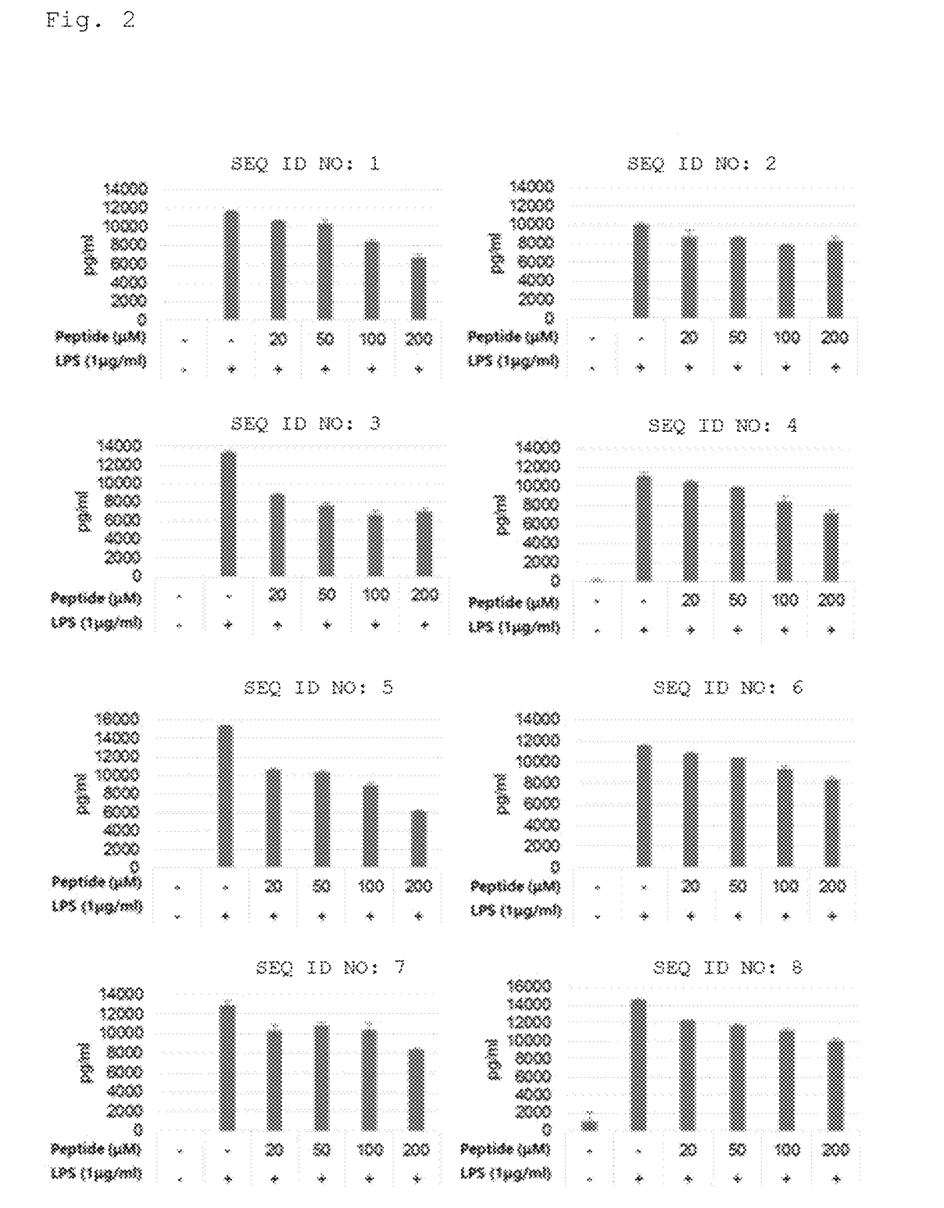
FIG. 2 show the results of measurement of the amount of produced cytokine interleukin 6 after treatment of RAW 264.7 cells with different concentrations of the peptides of SEQ ID NOS: 1 to 8 and induction of inflammation by LPS.

FIG. 2 is a graph showing a change in the amount of interleukin 6 produced by the peptides of SEQ ID NOS: 1 to 8. The concentration of IL-6 was increased in RAW 264.7 macrophages supplemented with LPS, but the production of interleukin 6 was decreased in a concentration-dependent manner in a medium treated with LPS and the peptides of SEQ ID NOs: 1 to 8. This means that the peptides of SEQ ID NOS: 1 to 8 were effective in reducing inflammation.

Test Example 3: Evaluation of Differentiation Capability from Mesenchymal Stem Cells to Chondrocytes by Bifunctional Peptide Having Capability to Reduce Inflammation and Capability to Facilitate Differentiation of Stem Cells into Chondrocytes In order to identify the ability of the bifunctional peptide to differentiate into chondrocytes from stem cells, the peptides of SEQ ID NOS: 1 to 8 were each dissolved in PBS at a concentration of 1 mM. $1\times10^6$ cells/mL of the cultured mesoderm-derived stem cells were seeded in a 24-well plate, treated with 100 μm of each of the peptides of SEQ ID NOS: 1 to 8, and further treated therewith whenever the medium was replaced. The cells were cultured for 21 days in a cartilage differentiation medium containing DMEM-HG, sodium pyruvate, 100 nM dexamethasone, 20 μg/mL proline, 37.5 μg/mL ascorbic 2-phosphate, 1% PS, 10 ng/mL TGF-β1, 1% FBS, and 1× insulin-transferrin-selenium (ITS+), and then the capability to differentiate into chondrocytes was evaluated. Each of the cells was disrupted using TRIzol reagent, and total RNA was extracted. The extracted RNA was reverse-transcribed into cDNA and amplified through a polymerase chain reaction. Collagen type II and Aggrecan were used to identify cartilage differentiation. 1 μl of each of 10 μM type collagen II, aggrecan, and GAPDH gene sense and antisense primers, 25 μl of Power CYBR Green PCR master mix (Invitrogen) and 22 μl of DW were added to 1 μl of the cDNA template to produce a sample, and the sample was measured using a StepOnePlus (Invitrogen). The nucleic acid sequences of the PCR primers used for the amplification of respective genes and the sizes of the PCR products are as follows.

```
Type II collagen
SEQ ID NO: 9:
forward primer:
5'-GGCAATAGCAGGTTCACGTACA-3'

SEQ ID NO: 10:
reverse primer:
5'-CGATAACAGTCTTGCCCCACTT-3'
Product size: 79 bp

Aggrecan
SEQ ID NO: 11:
forward primer:
5'-TCGAGGACAGCGAGGCC-3'
24-16

SEQ ID NO: 12:
reverse primer:
5'-TCGAGGGTGTAGCGTGTAGAGA-3'
Product size: 85 bp

GAPDH (glyceraldehyde-3-phosphate dehydrogenase)
SEQ ID NO: 13:
forward primer:
5'-ATGGGGAAGGTGAAGGTCG-3'

SEQ ID NO: 14:
reverse primer:
5'-TAAAAGCAGCCCTGGTGACC-3'
Product size: 119 bp
```

Figure 3:
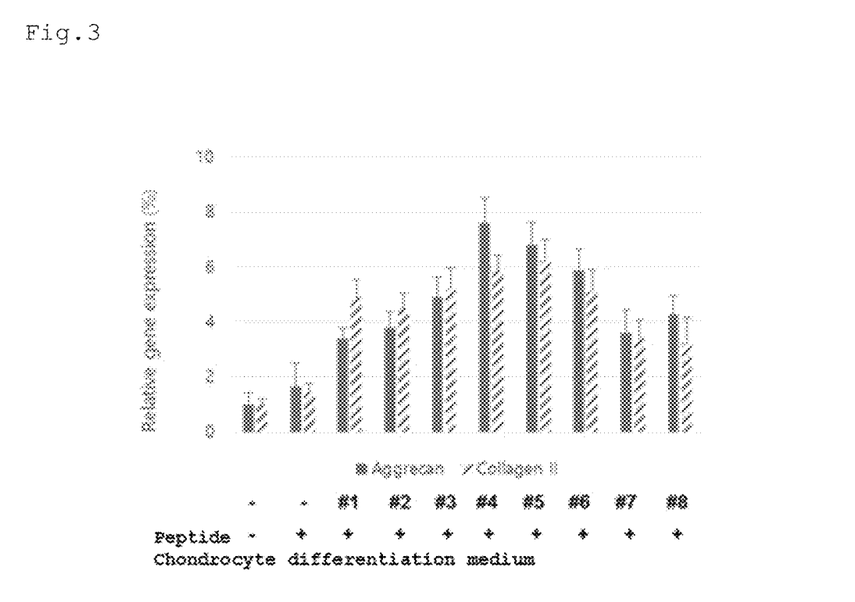
FIG. 3 show the expression levels of collagen type II and aggrecan genes measured using RT-PCR after treatment of mesenchymal stem cells (MSCs) with peptides of SEQ ID NOS: 1 and 8 and culture of the MSCs in a cartilage differentiation medium for 14 days.

The RT-PCR results are shown in FIG. 3. The expression of collagen type II and Aggrecan genes was increased when treated with each of the peptides of SEQ ID NOS: 1 to 8 in a cartilage differentiation medium. This means that stem cells differentiated into chondrocytes. It could be seen from this that the peptides of SEQ ID NOS: 1 to 8 were effective in facilitating the differentiation of stem cells into chondrocytes.

Although specific configurations of the present invention have been described in detail, those skilled in the art will appreciate that preferred embodiments of this description are given for illustrative purposes and should not be construed as limiting the scope of the present invention. Therefore, the substantial scope of the present invention is defined by the accompanying claims and equivalents thereto.

Advantageous Effects

The bifunctional peptide according to the present invention has a function of reducing inflammation by inhibiting the expression of HDAC1 and HDAC5 and the production of cytokine interleukin 6, and exerts an effect of facilitating differentiation of stem cells into chondrocytes by improving the expression of collagen type II and aggrecan, which are cartilage-cell-specific genes, when mesenchymal stem cells (MSCs) are treated with the bifunctional peptide. Thus, advantageously, the bifunctional peptide can be effectively used as a pharmaceutical composition for preventing or treating arthritis accompanied by inflammation and damage of cartilage tissue and a biomaterial, and can be easily applied to various surgical regenerative treatments including orthopedic treatments and can shorten the treatment period.

---

What is claimed is:

1. A method for treating arthritis accompanied by damage of cartilage tissue, said method comprising promoting the differentiation of stem cells into chondrocytes by administering a peptide represented by the amino acid sequence of any one of SEQ ID NOS: 4 to 6 to a subject in need thereof, said peptide functioning to regenerate cartilage tissue, and to reduce arthritis inflammation.

2. The method according to claim 1, wherein the peptide is prepared for injection or topical implantation.

3. The method according to claim 1, wherein the peptide is administered at a dose of 0.001 to 1,000 mg per 1 kg of a body weight of the subject.

4. A method for treating arthritis accompanied by damage of cartilage tissue, said method, comprising promoting the differentiation of stem cells into chondrocytes by administering a biomaterial for treating arthritis comprising a peptide represented by the amino acid sequence of any one of SEQ ID NOS: 4 to 6 to a subject in need thereof, said peptide functioning to regenerate cartilage tissue, and to reduce arthritis inflammation.

5. The method according to claim 4, wherein the biomaterial comprises any one selected from the group consisting of a barrier membrane, a porous scaffold, and an implant for bio-implant produced in the form of a gel.

6. The method according to claim 5, wherein the barrier membrane comprises any one selected from the group consisting of collagen, chitosan, gelatin, polylactide, polylactide glycolide and polycaprolactone.

7. The method according to claim 5, wherein the porous scaffold comprises any one selected from the group consisting of collagen, chitosan, gelatin, hyaluronic acid, alginic acid, chondroitin sulfate, polylactide, polylactide glycolide, and polycaprolactone.

8. The method according to claim 5, wherein the gel comprises any one selected from the group consisting of collagen, chitosan, gelatin, hyaluronic acid, alginic acid, poloxamer, propylene glycol, propylene glycol alginate, chondroitin sulfate and glycosaminoglycan.

9. The method according to claim 4, wherein the peptide is present at a dose of 1 to 50 mg per 1 g of the biomaterial.

* * * * *

UNITED STATES PATENT AND TRADEMARK OFFICE
CERTIFICATE OF CORRECTION

PATENT NO. : 11,365,218 B2
APPLICATION NO. : 16/882648
DATED : June 21, 2022
INVENTOR(S) : Yoon Jeong Park It is certified that error appears in the above-identified patent and that said Letters Patent is hereby corrected as shown below:

In the Specification

Column 6, Lines 13-14, "succinimidyl-4-[N-maleimidomethylcyclohexanel-carboxy-[6-amidocaproate]]" should be -- succinimidyl-4-[N-maleimidomethylcyclohexane1-carboxy-[6-amidocaproate]] --.

Column 8, Line 10, "after hours" should be -- after 16 hours --.

Column 8, Lines 16-17, "Tris-HCl" should be -- Tris•HCl --.

Column 8, Line 52, "$5 \times 10^3$" should be -- $5 \times 10^5$ --.

Column 9, Line 31, "10 μM" should be -- 10 pM --.

Signed and Sealed this
Sixteenth Day of August, 2022

Katherine Kelly Vidal
*Director of the United States Patent and Trademark Office*

SEQUENCE LISTING

```
<160> NUMBER OF SEQ ID NOS: 14

<210> SEQ ID NO 1
<211> LENGTH: 15
<212> TYPE: PRT
<213> ORGANISM: Artificial Sequence
<220> FEATURE:
<223> OTHER INFORMATION: bifunctional peptide

<400> SEQUENCE: 1

Gly Lys Cys Ser Thr Arg Gly Arg Lys Cys Cys Arg Arg Lys Lys
1               5                   10                  15

<210> SEQ ID NO 2
<211> LENGTH: 15
```

```
<212> TYPE: PRT
<213> ORGANISM: Artificial Sequence
<220> FEATURE:
<223> OTHER INFORMATION: bifunctional peptide

<400> SEQUENCE: 2

Gly Lys Cys Ser Thr Arg Gly Arg Lys Cys Met Arg Arg Lys Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: bifunctional peptide

<400> SEQUENCE: 3

Gly Lys Cys Ser Thr Arg Gly Arg Lys Met Cys Arg Arg Lys Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: bifunctional peptide

<400> SEQUENCE: 4

Gly Lys Cys Ser Thr Arg Gly Arg Lys Met Met Arg Arg Lys Lys
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: bifunctional peptide

<400> SEQUENCE: 5

Gly Lys Met Ser Thr Arg Gly Arg Lys Cys Cys Arg Arg Lys Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: bifunctional peptide

<400> SEQUENCE: 6

Gly Lys Met Ser Thr Arg Gly Arg Lys Met Cys Arg Arg Lys Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: bifunctional peptide

<400> SEQUENCE: 7

Gly Lys Met Ser Thr Arg Gly Arg Lys Cys Met Arg Arg Lys Lys
1               5                   10                  15

<210> SEQ ID NO 8
<211> LENGTH: 15
<212> TYPE: PRT
```

```
<213> ORGANISM: Artificial Sequence
<220> FEATURE:
<223> OTHER INFORMATION: bifunctional peptide

<400> SEQUENCE: 8

Gly Lys Met Ser Thr Arg Gly Arg Lys Met Met Arg Arg Lys Lys
1               5                   10                  15

<210> SEQ ID NO 9
<211> LENGTH: 22
<212> TYPE: DNA
<213> ORGANISM: Artificial Sequence
<220> FEATURE:
<223> OTHER INFORMATION: bifunctional peptide

<400> SEQUENCE: 9
ggcaatagca ggttcacgta ca                                              22

<210> SEQ ID NO 10
<211> LENGTH: 22
<212> TYPE: DNA
<213> ORGANISM: Artificial Sequence
<220> FEATURE:
<223> OTHER INFORMATION: bifunctional peptide

<400> SEQUENCE: 10
cgataacagt cttgccccac tt                                              22

<210> SEQ ID NO 11
<211> LENGTH: 17
<212> TYPE: DNA
<213> ORGANISM: Artificial Sequence
<220> FEATURE:
<223> OTHER INFORMATION: bifunctional peptide

<400> SEQUENCE: 11
tcgaggacag cgaggcc                                                    17

<210> SEQ ID NO 12
<211> LENGTH: 22
<212> TYPE: DNA
<213> ORGANISM: Artificial Sequence
<220> FEATURE:
<223> OTHER INFORMATION: bifunctional peptide

<400> SEQUENCE: 12
tcgagggtgt agcgtgtaga ga                                              22

<210> SEQ ID NO 13
<211> LENGTH: 19
<212> TYPE: DNA
<213> ORGANISM: Artificial Sequence
<220> FEATURE:
<223> OTHER INFORMATION: bifunctional peptide

<400> SEQUENCE: 13
atggggaagg tgaaggtcg                                                  19

<210> SEQ ID NO 14
<211> LENGTH: 19
<212> TYPE: DNA
<213> ORGANISM: Artificial Sequence
<220> FEATURE:
<223> OTHER INFORMATION: bifunctional peptide
```

```
<400> SEQUENCE: 14
atggggaagg tgaaggtcg                                                    19
```